United States Patent [19]

Hermes

[11] Patent Number: 4,917,921
[45] Date of Patent: Apr. 17, 1990

[54] ANTITHROMBOGENIC AND ANTIBIOTIC COMPOSITION AND METHODS OF PREPARATION THEREOF

[75] Inventor: Robert E. Hermes, Los Alamos, N. Mex.

[73] Assignee: The United States of America as represented by the United States Department of Energy, Washington, D.C.

[21] Appl. No.: 184,545

[22] Filed: Apr. 20, 1988

[51] Int. Cl.$^4$ .................... B05D 1/18; C08F 228/06
[52] U.S. Cl. .................. 427/430.1; 522/167; 522/168; 427/385.5; 526/256
[58] Field of Search ............... 526/256; 522/127, 167, 522/168; 427/385.5, 430.1; 137/54.1

[56] References Cited

U.S. PATENT DOCUMENTS 2,556,419  6/1951  Emerson et al. .................. 526/256
2,876,216  3/1959  Anderson et al. ................. 526/256

OTHER PUBLICATIONS

C. H. Bamford, I. P. Middleton, and Y. Satake, "Grafting and Attachment of Anti-Platelet Agents to Poly(Ether-Urethanes)" Bioch. Biophys. Acta, 886, 109 (1986).

J. Bourdais, "Copolymerization of Sodium Vinyl Sulfonate," Comptes Rendus, 246, 2374 (1958).

J. Bourdais, "Copolymers of N-Vinyl Pyrrolidone and Vinyl Sulfuric Acid," Comptes Rendus, 251, 1636 (1960).

R. Apitz-Castro, S. Cabrera, M. R. Cruz, E. Ledezma, and M. K. Jain, "Effects of Garlic Extract and of Three Pure Components Isolated from it on Human Platelet Aggregation, Arachidonate Metabolism, Release Reaction and Platelet Ultrastructure," Thrombosis Research, 32, 155 (1983).

E. Block, S. Ahmad, J. L. Catalfamo, M. K. Jain, and R. Apitz-Castro, "Antithrombotic Organosulfur Compounds from Garlic: Structural, Mechanistic, and Synthetic Studies," J. Am. Chem. Soc., 108, 7045 (1986).

H. Bock, S. Mohmand, T. Hirabayashi, and A. Semkow, "Thioacrolein," J. Am. Chem. Soc., 104, 312 (1982).

Primary Examiner—Joseph L. Schofer
Assistant Examiner—Peter F. Kulkosky
Attorney, Agent, or Firm—Samuel M. Freund; Paul D. Gaetjens; William R. Moser

[57] ABSTRACT

Antithrombogenic and antibiotic composition of matter and method of preparation thereof. A random copolymer of a component of garlic and a biocompatible polymer has been prepared and found to exhibit antithrombogenic and antibiotic properties. Polymerization occurs selectively at the vinyl moiety in 2-vinyl-4H-1,3-dithiin when copolymerized with N-vinyl pyrrolidone.

14 Claims, 3 Drawing Sheets

ANTITHROMBOGENIC AND ANTIBIOTIC COMPOSITION AND METHODS OF PREPARATION THEREOF

The U.S. Government has rights in this invention pursuant to Contract No. W-7405-ENG-36 between the U.S Department of Energy and the University of Calif.

BACKGROUND OF THE INVENTION

The Present invention relates generally to biocompatible materials, and more particularly to antithrombogenic and antibiotic compositions for use as coatings for artificial prostheses and implants which remain in contact with blood or other physiological fluids.

Garlic (Allium sativum) has been employed as a folk medicine for thousands of years for the prevention of stroke, coronary thrombosis, and atherosclerosis, as well as for treatment of various diseases including infections and vascular disorders. Garlic extracts have also been reputed to reduce serum cholesterol levels and to increase blood coagulation time. More recently, some components of garlic have been shown to have antibiotic properties, while others are potent inhibitors of platelet aggregation, one of the first steps in blood clot formation or thrombosis.

The need for improving the biocompatibility of synthetic materials intended for medical uses is considerable. One approach has been to increase the hydrophilicity of polymer surfaces by chemically grafting water swellable polymers. The known antithrombotic action of specific compounds has been utilized in attempts to prepare nonthrombogenic surfaces either by chemically binding such materials to surfaces, or by physically incorporating them into bulk polymers.

The grafting of polymeric materials to one another is well understood (See, e.g., "Grafting and Attachment of Anti-platelet Agents to poly(Ether-Urethanes)" by C. H. Bamford, I. P. Middleton, and Y. Satake, Bioch. Biophys. Acta 886. 109 (1986).), so that any molecule into which a polymerizable double bond may be introduced may, in principle, be attached to a polymer chosen as the material of fabrication for a prosthesis or implant. An alternative is to copolymerize a molecule already possessing a polymerizable olefinic bond (and having desirable antithrombogenic properties) with the prosthesis or implant fabrication polymer, and to graft the resulting material to this fabrication polymer. It is important that the antithrombogenic compound have antibacterial and antifungal (antibiotic) activity as well, since infection is a significant risk in any implant surgery. Past efforts in the production of blood compatible polymers have also included the incorporation of anticoagulants into polymeric matrices for controlled release of the active component. Controlled release methods depend upon diffusion and/or hydrolysis of the active component from the polymeric matrix for the nonthrombogenic effect.

N-vinyl pyrrolidone is a well-known monomeric precursor to poly(N-vinyl pyrrolidone), a water soluble polymer. Copolymerization of this material with sodium vinyl sulfonate and with vinyl sulfuric acid have been reported by J, Bourdais in "Chimie Macromoleculaire. -Copolymerisation du vinylsufonate de sodium. " Comptes Rendus 246, 2374 (1958), and in "Macromolecules. -Copolymeres de N-vinylpyrrolidone et de sulfate acide de vinyle." Comptes Rendus 251, 1636 (1960) by the same author, respectively. That is, successful attempts to synthesize polymeric analogs of heparin, a naturally occurring anticoagulant containing sulfonate groups have been reported, but biological activity of the resulting compounds were not addressed.

More recently others have reported the covalent attachment of a prostaglandin analog (BW 245) to poly(ether-urethanes), poly(ethylene glycol), dextran, and poly(N-vinyl pyrrolidone). The BW 245 was incorporated in side-chains in the polymers by copolymerization of appropriate methacrylate esters of BW 245, and attached in terminal positions of vinyl polymers using haloesters thereof. Such polymers were shown to be effective inhibitors of platelet aggregation in platelet rich plasma using adenosine diphosphate (ADP) induced aggregation.

Detailed accounts of antithrombotic organosulfur compounds found in garlic extracts mention the discovery of a number of platelet aggregation inhibitors (See, e.g., R. Apitz-Castro, S. Cabrera, M. R. Cruz, E. Ledezma, and M. K. Jain, "Effects of Garlic Extract and of Three pure Components Isolated from it on Human platelet Aggregation, Arachidonate Metabolism, Release Reaction and platelet Ultrastructure," Thrombosis Research 32, 155 (1983) and E. Block, S. Ahmad, J. L. Catalfamo, M. K. Jain, and R. Apitz-Castro, "Antithrombotic Organosulfur Compounds from Garlic: Structural, Mechanistic, and Synthetic Studies," J. Am. Chem. Soc. 108, 7045 (1986). The compounds investigated were found generally to exhibit antibacterial and antifungal properties as well. Of these, 2-vinyl-4H-1,3-dithiin was reported to have only moderate activity. Synthetic methods are also available for the production of this dithiin monomer, the simplest involving the vacuum thermolysis of diallyl sulfide to produce dimers of thioacrolein, one of which is the dithiin compound (See, e.g., H. Bock, S. Mohmand, T. Hirabayashi, and A. Semkow, "Thioacrolein," J. Am. Chem. Soc. 104, 312 (1982). To date, homopolymerization or copolymerization of this vinyl organosulfur compound with other vinyl monomers has not been reported. Moreover, it was unknown if the biological activity of this species would be destroyed during the polymerization process. Additionally, such compounds often cannot be polymerized, since the presence of sulfur atoms assists in inhibition of polymerization.

Accordingly, an object of the present invention is to provide a biocompatible composition of matter having antithrombogenic and antibiotic properties for use in biomedical applications where polymeric surfaces are in direct contact with blood or physiological fluids.

Another object of my invention is to prepare a copolymer having antithrombogenic and antibiotic properties for use in biomedical applications where polymeric surfaces are in direct contact with blood or physiological fluids.

Yet another object of my invention is to provide a biocompatible composition of matter that may be used as a surface modification material for preformed polymeric articles such as artificial prostheses and implants in contact with blood or physiological fluids such that the resulting prostheses and implants have antithrombogenic and antibiotic properties.

Additional objects, advantages and novel features of the invention will be set forth in part in the description which follows, and in part will become apparent to those skilled in the art upon examination of the following or may be learned by practice of the invention. The objects and advantages of the invention may be realized and attained by means of the instrumentalities and combinations particularly pointed out in the appended claims.

SUMMARY OF THE INVENTION

To achieve the foregoing and other objects and in accordance with the purposes of the present invention, as embodied and broadly described herein, the composition of matter of this invention includes a copolymer of 2-vinyl-4H-1,3-dithiin and the monomer of a biocompatible polymer. It is preferred that the monomer of the biocompatible polymer includes N-vinyl pyrrolidone.

In a further aspect of the present invention, in accordance with its objects and purposes, the method of preparation of a biocompatible material having antithrombogenic and antibiotic properties hereof includes the steps of dissolving the monomer of a vinyl polymer, a chosen quantity of 2-vinyl-4H-1,3-dithiin, and a chosen quantity of free-radical initiator in a common solvent therefor, thereby forming a solution, purging the solution with inert gas, heating the solution for a period sufficient to achieve significant reaction, and precipitating the polymeric material. It is preferred that the monomer of the vinyl polymer includes monomers of biocompatible polymers. Preferably, the monomer of the biocompatible polymer includes N-vinyl pyrrolidone. preferably also. between about 0.5 and 50 mole percent of 2-vinyl-4H-1,3-dithiin is employed. It is also preferred that the heating step is carried out at between 25° and 60°. Preferably also, between about 0.5 and 2 mole percent of free-radical initiator is employed.

In yet a further embodiment of my invention, in accordance with its objects and purposes, the method for preparing coated polymeric articles having antithrombogenic and antibiotic properties hereof also includes dissolving a chosen quantity of the monomer of a vinyl polymer, a chosen quantity of 2-vinyl-4H-1,3-dithiin, and a chosen quantity of photochemical initiator in a common solvent therefor, thereby forming a solution, placing the polymeric article to be coated in the solution, purging the solution with an inert gas, and irradiating the solution to generate free radicals from the photochemical initiator in sufficient quantities to achieve significant reaction. It is preferred that the monomer of the vinyl polymer includes monomers of biocompatible polymers. Preferably, also the monomer of the biocompatible polymer includes N-vinyl pyrrolidone.

Benefits and advantages of the present invention include the simple fabrication of articles and the coating of polymeric articles to produce articles having antithrombogenic and antibiotic properties from inexpensive and readily synthesized starting materials.

BRIEF DESCRIPTION OF THE DRAWINGS

The accompanying drawings, which are incorporated in and form a part of the specification, illustrate an embodiment of the present invention and, together with the description, serve to explain the principles of the invention. In the drawings.

DETAILED DESCRIPTION OF THE PREFERRED EMBODIMENTS

Figure 1A:
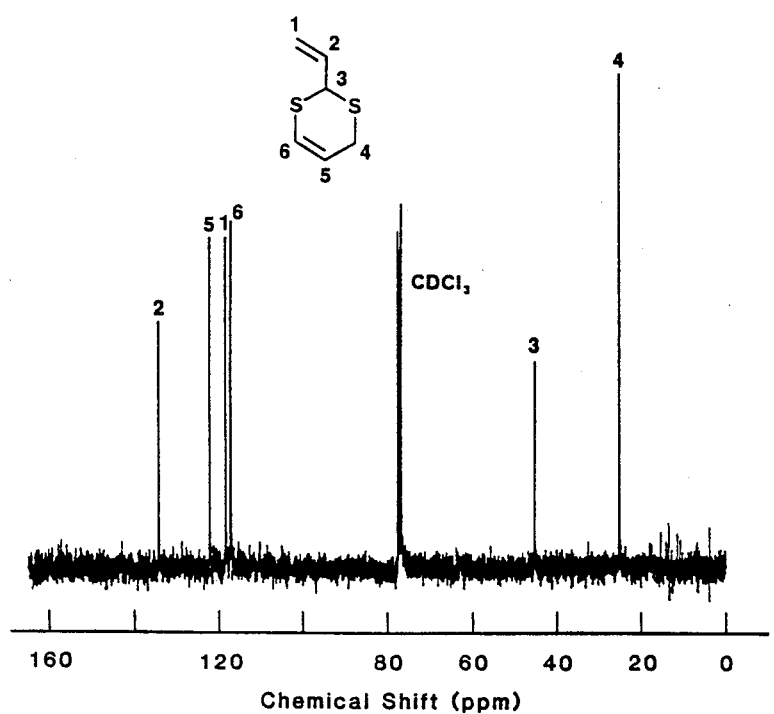
FIG. 1a shows the $^{13}C$ NMR spectrum for the dithiin monomer in a solution of $CDCl_3$. Peaks corresponding to carbon atoms in the molecule are identified with the same numbers used to identify the carbon atoms.

Briefly, the present invention includes a polymeric antibiotic, and platelet aggregation inhibitor obtained from the copolymerization of 2-vinyl-4H-1,3-dithiin and N-vinyl pyrrolidone. The dithiin compound constitutes between 0.5 and 50 mole percent of the copolymer. The biological activity of the polymer derives from the dithiin compound which is a monomeric organosulfur compound naturally found in garlic, or which can be readily synthesized from commercially available starting material. If the dithiin compound is restricted to less than approximately 10 mole percent of the copolymer. The water solubility characteristics of the copolymer are similar to those of poly(N-vinyl pyrrolidone) (PVP). The inactive component is not limited to PVP, but may include any water-soluble, water-swellable, or water-insoluble polymer, depending upon the application. The copolymer is readily prepared by free-radical polymerization procedures in solution or in bulk to produce product material having a molecular weight between about 2000 and 500,000, and is suitable for applications in environments where there is continuous contact with physiological fluids. Thermal initiation using free-radical initiators, photochemical initiation using photoinitiators, or chemical initiation by group transfer polymerization with activated methyl methacrylate, for example, are all routes for easily generating the copolymer. Graft polymerizations of the copolymer onto other polymeric substrates may also be possible. Copolymer purification may be accomplished using multiple precipitations from a solvent into a nonsolvent such as diethyl ether.

The copolymer was found to have approximately one-third of the antiaggregation ability of the dithiin monomer (per mole basis of dithiin moiety) and significant antibacterial activity against *Staphylococcus aureus*. Additionally, as the percentage of dithiin increases, the water solubility decreases. Copolymers with 6-12% of dithiin incorporation are soluble in ethyl alcohol, while higher percentages are soluble only in mixtures of benzene and tetrahydrofuran. Such copolymers are useful as water insoluble coatings on other polymeric substrates.

Having generally described the present invention, the following specific examples are given as a further illustration thereof.

EXAMPLE I

The 2-vinyl-4H-1,3-dithiin monomer was prepared by the large scale vacuum thermolysis of commercially available diallyl sulfide in a manner similar to that disclosed in Bock et al., supra. Separate runs of 20 each were combined to produce about 100 g of crude product. Residual diallyl sulfide was removed by vacuum distillation leaving a dark brown liquid product in 20% yield The mixture of products was separated using preparative scale liquid chromatography on a silica gel column with 40% methylene chloride/hexanes elution solvent at a flow rate of 4.0 mL/min. Solvent removal from each fraction resulted in purified products. The second fraction contained the dithiin monomer with an overall Yield of 5%. Purity and compound identification were checked by gas chromatography/mass spectrometry and carbon-13 NMR.

EXAMPLE II

A chosen quantity of purified dithiin monomer was added to a test tube (2–16 mole percent) containing N-vinyl pyrrolidone (0.005 moles) and 6.0 mL of benzene for a total concentration of about 10% weight-/volume. A 0.5%–2% molar weight of the azo initiator, AIBN, 2,2'-azobis(isobutyronitrile) (Vazo-64 from Dupont) was added. The tube was capped with a rubber septum and purged with dry nitrogen for 5 minutes before immersing the tube into a thermostated oil bath held at 60° C. polymerization occurred over a period of 2–3 days. Crude polymer was obtained by precipitation in 20 volumes of diethyl ether in yields ranging from 7% to 30%.

Using 2.0 mole percent of dithiin, a copolymer was prepared having 2.3 mole percent incorporation of the dithiin moiety in the copolymer as determined by elemental analysis. The yield was approximately 30%. Table I shows results for several polymerization reactions.

TABLE I

| POLYMER | % yield | mole % a. dithiin | b. $[\eta]$(dL/g) | c. $M_v$ |
|---|---|---|---|---|
| A | 30 | 2.3 | | |
| B | 21 | 5.4 | | |
| C | 15 | 7.0 | 0.049 | 6H |
| D | 7 | 8.5 | 0.062 | 8K |
| E | 8 | >10 | 0.057 | 7K |
| PVP | 89 | none | 0.400 | 150K | a. calculated from elemental analysis
b. intrinsic viscosity in chloroform at 25°
c. approximate value based on Mark-Houwink constants for poly(N-vinyl pyrrolidone) homopolymer Although this composition afforded the highest yield, the copolymer was also prepared using 2% molar weight of 2,2'-azobis(methyl isobutyrate) (V-601 from Wako Chemical, Inc.) as the initiator. With similar proportions of the other reagents to those described in Example II, all of the conditions of the synthesis remaining the same. Since benzene and cyano groups interfere with the NMR analysis, reprecipitation of the product from chloroform solvent yielded pure polymer with no benzene. The V-601 initiator fragment has no cyano groups but rather has a methyl ester which does not interfere in the vinyl region of the NMR spectrum.

Figure 1B:
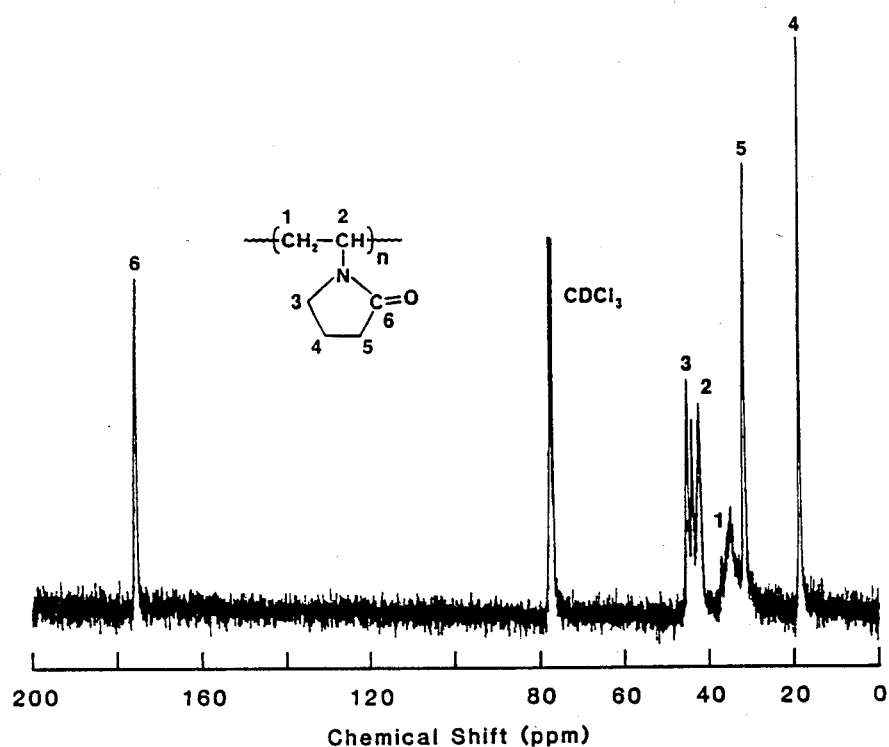
FIG. 1b shows the $^{13}C$ NMR spectrum for the PVP homopolymer dissolved in $CDCl_3$. Notice the complete unsaturated carbon-carbon bond signatures.
Figure 1C:
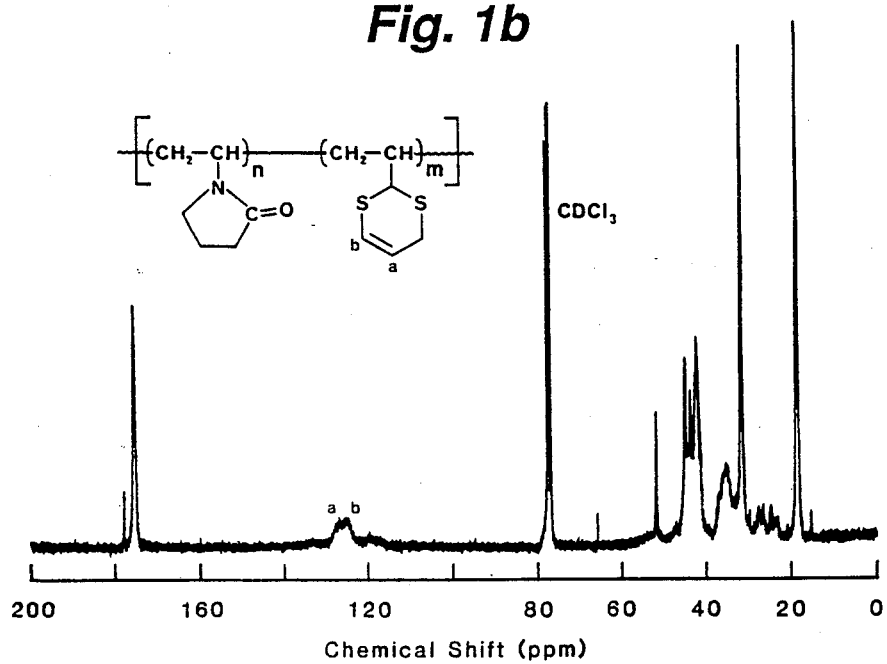
FIG. 1c shows the $^{13}C$ NMR spectrum for reprecipitated poly(2-vinyl-4H-1,3-dithiin-co-N-vinyl pyrrolidone) dissolved in $CDCl_3$. Two small broadened peaks are present in the unsaturated portion of the spectrum, and represent the resonances due to the ring unsaturation in the dithiin moiety.

Reference will now be made in detail to the present preferred embodiments of the invention, an example of which is illustrated in the accompanying drawings. Turning now to the Figures, FIG. 1a shows the $^{13}C$ NMR spectrum for the dithiin monomer in a solution of $CDCl_3$. Peaks corresponding to carbon atoms in the molecule are identified with the same numbers as are used to identify the carbon atoms. Notice the strong peaks corresponding to unsaturated carbon-carbon bonds in the ion between 115 and 135 ppm. FIG. 1b shows the $^{13}C$ NMR spectrum for the PVP homopolymer dissolved in $CDCl_3$. Notice the complete absence of unsaturated carbon-carbon bond signatures. Finally, FIG. 1c shows the $^{13}C$ NMR spectrum for reprecipitated poly(2-vinyl-4H-1,3-dithiin-co-N-vinyl pyrrolidone) dissolved in $CDCl_3$. Two small broadened peaks are present in the unsaturated portion of the spectrum indicating that the dithiin moiety is randomly incorporated in a polymer. These features are not due to either benzene or cyano groups, which have resonances in this region, since the copolymer was prepared using 2,2'-azobis(methyl isobutyrate), which does not contain cyano groups, and the copolymer was reprecipitated from chloroform solutions. The vinyl carbons are clearly absent, rather, only the unsaturated carbons in the ring appear in the spectrum, demonstrating that polymerization has occurred exclusively at the vinyl double bond to generate saturated carbons in the backbone.

Copolymers prepared having 7.0 and 8.5% incorporation of the dithiin moiety in the copolymer, as determined by elemental analysis, and reprecipitated from chloroform, were used in platelet aggregation studies. Platelet rich plasma (PRP) was prepared from citrated human venous blood by centrifugation at 250 g for 10 min. The supernatant was collected and confirmed to contain about 250,000 platelets/$mm^3$ using a Coulter counter. An aliquot (0.8 ml) was added to each of several test tubes according to the procedure recommended by the manufacturer of the platelet aggregometer employed (Chrono-Log Corp., Havertown, PA 19083). The impedance method Was used to obtain quantitative results.

Figure 2:
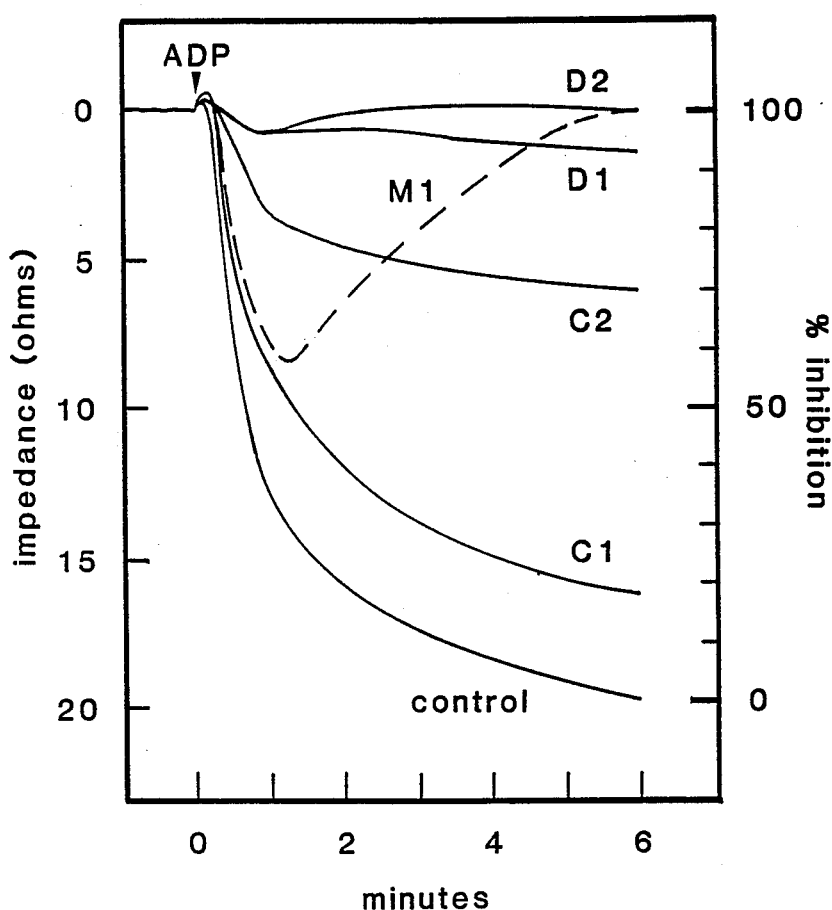
FIG. 2 shows ADP platelet aggregation response curves for two copolymers prepared according to the teachings of the present invention in two concentrations in saline solution, for the dithiin monomer in saline solution, and for a saline control.

Table II and FIG. 2 show the platelet aggregation investigation results at two different concentrations of each copolymer investigated. The polymeric compositions employed are labeled as in Table I hereof; that is, two concentrations of each of polymers C and D described in Table I were tested for activity in inhibiting platelet aggregation, as was the dithiin monomer. FIG. 2 shows platelet aggregation response curves labeled according to the species tested. The control curve was generated by incubating PRP for 6 min. with 0.2 mL of saline solution before the addition of 50 μL of ADP reagent from Sigma Chemical Corp. Complete aggregation was achieved after about 6 min.

TABLE II

| substrate | molar conc. $\times 10^2$ | molar eq. dithiin $\times 10^3$ | % inhibition |
|---|---|---|---|
| control | saline | none | 0 |
| C1 | 5.3 | 3.7 | 18 |
| C2 | 8.5 | 5.9 | 70 |
| D1 | 7.7 | 6.6 | 92 |
| D2 | 10.3 | 8.8 | 100 |
| M1 | .25 | 2.5 | 100 |

The curve for the monomer (M1) was obtained from PRP incubated for 8 min. with 2-vinyl-4H-1,3-dithiin at a molar concentration of $2 \times 10^{-3}$ and shows the typical behavior for monomeric species in that deaggregation and subsequent complete inhibition of aggregation occurs after the addition of ADP reagent induces some initial aggregation. The homopolymer of N-vinyl pyrrolidone was also tested at a molar concentration of approximately $3 \times 10^{-2}$ and found to have a similar effect to that of the control.

The copolymer having a 8.8 mole percent incorporation of dithiin moiety in the copolymer (D) was tested for antibiotic activity using the Kirby-Bauer disk sensitivity method (A. W. Bauer et al. "Antibiotic Testing by a Standardized Single Disk Method," Am. J. Clin. Pathol. 45, 493 (1966) where surfaces of separate Mueller-Hinton agar plates were inoculated with the copolymer. Activity was compared with PVP homopolymer, the dithiin monomer, and the standard antibiotic, norfloxacin. Norfloxacin and dithiin monomer showed inhibition of growth for most *Escherichia coli* and *Staphylococcus aureus*. The saline and PVP homopolymer controls had no activity. The copolymer had selected antibiotic activity against *Staphylococcus aureus* and was about 12 times more effective than the dithiin monomer (per mole percent of dithiin moiety). This selective activity is significant since *Staphylococcus aureus* is the pathogenic organism generally associated with infections of the skin, while *Escherichia coli* is a bacterium present in the normal flora of the intestine. The saline solution used to treat the challenge disks was analyzed using gas chromatography mass spectrometry and was found to contain no traces of the monomeric species which, if present, might cause a false reading in the sensitivity testing.

Using the method described in Example II with 9.5 mole percent dithiin a copolymer was prepared in 63% yield having about 16.4 mole percent of the dithiin moiety incorporated into the copolymer as was determined by elemental analysis. The resulting copolymer was found to be soluble in a mixture of benzene and tetrahydrofuran and is suitable as a coating for other matrices. That is, coated polymeric articles having antithrombogenic and antibiotic properties may be prepared by dissolving a chosen quantity of the monomer of a vinyl polymer, a chosen quantity of 2-Vinyl-4H-1,3-dithiin, and a chosen quantity of photochemical initiator in a common solvent therefor, thereby forming a solution, placing the polymeric article to be coated in the solution, purging the solution with an inert gas, and irradiating the solution to generate free radicals from the photochemical initiator in sufficient quantities to achieve covalent graft attachment to the polymeric article. Moreover, such coated articles might also be prepared by dissolving previously prepared copolymer in a solvent, placing a polymeric article to be coated in the resulting solution, and removing the polymeric article to be coated at such a rate as to allow evaporation of the resulting solution, thereby forming a physical coating of the article with a film of the biologically active copolymer.

The foregoing description of several preferred embodiments of the invention has been presented for purposes of illustration and description. It is not intended to be exhaustive or to limit the invention to the precise form disclosed, and obviously many modifications and variations are possible in the light of the above teaching. For example, other vinyl monomers could be copolymerized with the dithiin species to produce polymeric compositions having antithrombogenic and antibiotic properties. Additionally, different solvents, initiators and conditions of preparation may be utilized in the synthesis of the poly(2-vinyl-4H-1,3-dithiin-co-N-vinyl pyrrolidone). In fact, the copolymer can be prepared by polymerization in bulk of a mixture of the monomers and a free-radical initiator. The embodiments were chosen and described in order to best explain the principles of the invention and its practical application to thereby enable others skilled in the art to best utilize the invention in various embodiments and with various modifications as are suited to the particular use contemplated. It is intended that the scope of the invention be defined by the claims appended hereto.

What is claimed is:

1. An antithrombogenic and antibiotic composition of matter consisting essentially of a copolymer of 2-vinyl-4H-1,3-dithiin and N-vinyl pyrrolidone.

2. The composition of matter as described in claim 1, of 2-vinyl-4H-1,3-dithiin.

3. A method of preparation of a copolymer of 2-vinyl-4H-1,3-dithiin and N-vinyl pyrrolidone, said method comprising the steps of:
   a. Dissolving a chosen quantity of N-vinyl pyrrolidone iu a solvent forming a first solution;
   b. dissolving a chosen quantity of 2-vinyl-4H-1,3-dithiin in the first solution forming thereby a second solution;
   c. dissolving a chosen quantity of free-radical initiator in the second solution forming thereby a third solution;
   d. purging the third solution with inert gas;
   e. heating the third solution for a period sufficient to achieve significant reaction; and
   f. precipitating the resulting polymeric material.

4. The method as described in claim 3, wherein between about 0.5 and 50 mole percent of 2-vinyl-4H-1,3-dithiin is employed.

5. The method as described in claim 3, wherein said heating step is carried out at between 25° C. and 60° C.

6. The method as described in claim 3, wherein between about 0.5 and 2 mole percent of free-radical initiator is employed.

7. A method for preparing coated polymeric articles having antithrombogenic and antibiotic properties, said method comprising the steps of:
   a. dissolving a chosen quantity of N-vinyl pyrrolidone in a solvent forming a first solution;
   b. dissolving a chosen quantity of 2-vinyl-4H-1,3-dithiin in the first solution forming thereby a second solution;
   c. dissolving a chosen quantity of photochemical initiator in the second solution forming thereby a third solution;
   d. placing the polymeric article to be coated in the third solution;
   e. purging the third solution with an inert gas; and 8. A method of preparation of a copolymer of 2-vinyl-4H-1,3-dithiin and N-vinylpyrrolidone, said method comprising the steps of:
   a. dissolving the N-vinyl pyrrolidone, a chosen quantity of 2-vinyl-4H-1,3-dithiin, and a chosen quantity of free-radical initiator in a common solvent therefor, thereby forming a solution;
   b. purging the solution with inert gas;
   c. heating the solution for a period sufficient to achieve significant reaction; and
   d. precipitating the polymeric material.

9. The method as described in claim 8, wherein between about 0.5 and 50 mole percent of 2-vinyl-4H-1,3-dithiin is employed.

10. The method as described in claim 8, wherein said heating step is carried out at between 25° C. and 60° C.

11. The method as described in claim 8, wherein between about 0.5 and 2 mole percent of free-radical initiator is employed.

12. A method for preparing coated polymeric articles having antithrombogenic and antibiotic properties, said method comprising the steps of:
   a. dissolving a chosen quantity of N-vinyl pyrrolidone, a chosen quantity of 2-vinyl-4H-1,3-dithiin, and a chosen quantity of photochemical initiator in a common solvent therefor, thereby forming a solution;
b. placing the polymeric article to be coated in the solution;
c. purging the solution with an inert gas; and
d. irradiating the solution to generate free-radicals from the photochemical initiator in sufficient quantities to achieve covalent graft attachment to the polymeric article.

13. A method for preparing coated polymeric articles having antithrombogenic and antibiotic properties, said method comprising the steps of:
a. dissolving a chosen quantity of poly(2-vinyl-4H-1 3-dithiin-co-N-vinyl pyrrolidone) in a solvent, thereby forming a solution;
b. placing the polymeric article to be coated in the solution; and
c. removing the polymeric article at such a rate as to allow evaporation of the solvent and the physical coating of the polymeric article with a film of poly(2-vinyl-4H-1,3-dithiin-co-N-vinyl pyrrolidone).

14. A method of preparation of a copolymer of 2-vinyl-4H-1 3-dithiin and N-vinyl pyrrolidone, said method comprising the steps of:
a. mixing chosen quantities of 2-vinyl-4H-1,3-dithiin, N-vinyl pyrrolidone, and a free-radical initiator; and
b. activating the free-radical initiator, thereby causing polymerization in bulk to occur.

* * * * *